United States Patent
Kundu et al.

(10) Patent No.: US 9,322,008 B2
(45) Date of Patent: Apr. 26, 2016

(54) MUTANTS OF L-ASPARAGINASE

(75) Inventors: Bishwajit Kundu, New Delhi (IN); Saurabh Bansal, New Delhi (IN); Prashant Mishra, New Delhi (IN)

(73) Assignees: Indian Institute of Technology, New Delhi (IN); Department of Biotechnology, Ministry of Science and Technology, New Delhi (IN)

( * ) Notice: Subject to any disclaimer, the term of this patent is extended or adjusted under 35 U.S.C. 154(b) by 210 days.

(21) Appl. No.: 13/819,702

(22) PCT Filed: Sep. 1, 2011

(86) PCT No.: PCT/IB2011/002018
§ 371 (c)(1),
(2), (4) Date: Aug. 8, 2013

(87) PCT Pub. No.: WO2012/028945
PCT Pub. Date: Mar. 8, 2012

(65) Prior Publication Data
US 2013/0330316 A1 Dec. 12, 2013

(30) Foreign Application Priority Data
Sep. 1, 2010 (IN) .......................... 2090/DEL/2010

(51) Int. Cl.
*C12N 9/82* (2006.01)
*A61K 38/46* (2006.01)
*A23L 1/015* (2006.01)

(52) U.S. Cl.
CPC ................ *C12N 9/82* (2013.01); *A23L 1/0153* (2013.01); *A61K 38/46* (2013.01); *C12Y 305/01001* (2013.01)

(58) Field of Classification Search
None
See application file for complete search history.

(56) References Cited

U.S. PATENT DOCUMENTS

2011/0052758 A1  3/2011  Greiner-Stoeffele et al.

FOREIGN PATENT DOCUMENTS

WO  WO-2008/151807  12/2008

OTHER PUBLICATIONS

GenBank, Accession No. NC_003413.1, 2010, www.ncbi.nlm.nih.gov.*
Yun et al., Crystal structure and allosteric regulation of the cytoplasmic *Escherichia coli* L-asparaginase I, J. Mol. Bio., 2007, 369, 794-811.*
Uniprot, Accession No. P0A962, Aug. 2010, www.uniprot.org.*
Avramis et al., "A randomized comparison of native *Escherichia coli* asparaginase and polyethylene glycol conjugated asparaginase for treatment of children with newly diagnosed standard-rick acute lymphoblastic leukemia: a Children's Cancer Group study," Blood (2002) 99(6):1986-1994,1531.
Bansal et al., "Hyperthermophilic asparaginase mutants with enhanced substrate affinity and antineoplastic activity: structural insights on their mechanism of action," Faseb J (2012) 26(3):1161-1171.
Bansal et al., "Structural stability and functional analysis of L-asparaginase from Pyrococcus furiosus," Biochemistry (Mosc) (2010) 75(3):375-381.
Broome, "Evidence that the L-Asparaginase Activity of Guinea Pig Serum is responsible for its Antilymphoma Effects," Nature (1961) 191:1114-1115.
Cao et al., "Chemical modification of enzyme molecules to improve their characteristics," Ann NY Acad Sci (1990) 613:460-467.
Cheung et al., "Antibody response to *Escherichia coli* L-asparaginase: Prognostic significance and clinical utility of antibody measurement," Am J Pediatr Hematol Oncol (1986) 8(2):99-104.
Derst et al., "Engineering the substrate specificity of *Escherichia coli* asparaginase II. Selective reduction of glutaminase activity by amino acid replacements at position 248," Protein Sci. (2000) 9(10):2009-2017.
Distasio et al., "Alteration in spleen lymphoid populations associated with specific amino acid depletion during L-asparaginase treatment," Cancer Res. (1982) 42(1):252-258.
International Preliminary Report on Patentability for PCT/IB2011/002018, corrected version, completed Dec. 20, 2012, 5 pages.
International Preliminary Report on Patentability for PCT/IB2011/002018 (replaced), completed Dec. 20, 2012, 5 pages.
International Search Report for PCT/IB2011/002018, mailed May 15, 2012, 5 pages.
Kidd et al., "Regression of transplanted lymphomas induced in vivo by means of normal guinea pig serum. I. Course of transplanted cancers of various kinds in mice and rats given guinea pig serum, horse serum, or rabbit serum," J Exp Med (1953) 98(6):565-582.
Li, et al., "Enhancing the thermostability of *Escherichis coli* L-asparaginase II by substitution with pro in predicted hydrogen-bonded turn structures," Enzyme and Microbial Technology (2007) 41(4):523-527.
Ohno et al., "Immunosuppressive effects of L-asparaginase," Cancer Res. (1970) 30(6):1605-1611.

(Continued)

*Primary Examiner* — Tekchand Saidha
*Assistant Examiner* — Todd M Epstein
(74) *Attorney, Agent, or Firm* — Morrison & Foerster LLP

(57) ABSTRACT

The present invention relates to a mutant of L-asparaginase enzyme characterized in having high thermostability, pH stability and no glutaminase activity useful for therapeutics and the process of preparing the same. The present invention specifically relates to mutants MTCC 5580, MTCC 5581 and MTCC 5582 characterized in having higher stability, no glutaminase activity etc., to allow their usage in the form of improved protein therapeutics.

15 Claims, 4 Drawing Sheets

(56) References Cited

OTHER PUBLICATIONS

Figure 1:
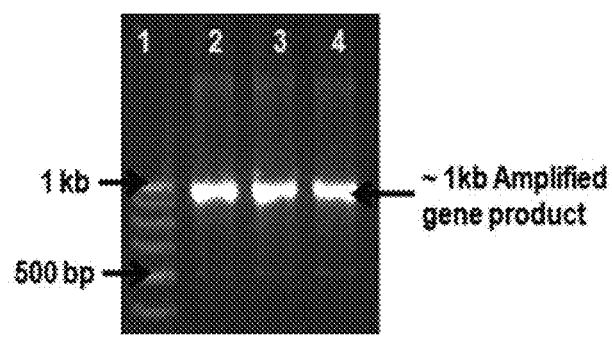

Schein et al., "The toxicity of *Escherichia coli* L-asparaginase," Cancer Res. (1969) 29(2):426-434.
Sequences 1, 2 from WO2008/151807.
Spiers et al., "Achromobacter L-glutaminase-L-asparaginase: human pharmacology, toxicology, and activity in acute leukemias," Cancer Treat Rep (1979) 63(6):1019-1024.
Written Opinion for PCT/IB2011/002018, mailed May 15, 2012, 5 pages.

* cited by examiner

MUTANTS OF L-ASPARAGINASE

CROSS REFERENCE TO RELATED APPLICATIONS

This application is a U.S. National Phase Application of International Application No. PCT/IB2011/002018, filed Sep. 1, 2011, which claims priority to and the benefit of Indian Patent Application No. 2090/DEL/2010 filed on Sep. 1, 2010, the entire contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720402000100SubstSeqList.txt, date recorded: Sep. 11, 2015, size: 25,455 bytes).

FIELD OF INVENTION

The present invention relates to a novel mutant of L-asparaginase enzyme characterized in having high thermostability, pH stability and no glutaminase activity useful for therapeutics and the process of preparing the same. The present invention specifically relates to mutant's MTCC 5580, MTCC 5581 and MTCC 5582 characterized in having higher stability, no glutaminase activity etc., to allow their usage in the form of improved protein therapeutics.

The present invention utilizes the asparaginase enzyme isolated from *Pyrococcus furiosus* and its three-dimensional structure to identify amino acid residues of relevance for improving the properties of the asparaginase enzyme.

The invention also relates to DNA sequences encoding such modified L-asparaginases and their production in a recombinant host cell.

More particularly, the invention relates to production of engineered L-asparaginase derivatives for use in pharmaceutical compositions for treating leukemic disorders. The engineered L-asparaginase may also be used for treating other diseases where L-asparagine depletion would be efficacious.

The invention also relates to the usefulness of the enzymes in food industries, such as starch based foodstuff, in inhibiting acrylamide synthesis.

BACKGROUND OF INVENTION

L-asparaginase is known to have therapeutic value in the treatment of Leukemia. Till date the enzymes obtained from *Escherichia coli*, and *Erwinia chrysanthemi* are being used for the same. L-asparaginase is an amidohydrolase which catalyzes L-asparagine into L-aspartic acid and ammonia. It plays a major role in the metabolism of L-asparagine in plants, animals and microorganisms. It has been energetically studied on its actual use as an antitumor agent since John G. Kidd et al had described the inhibitory action of L-asparaginase from guinea pig sera on lymphomas in "*The Journal of Experimental Medicine*", Vol. 98, pp. 565-582 (1953) and then evidenced by J. D. Broome et al. in "*Nature*", Vol. 191, pp. 1, 114-1, 115 (1961). It is now well established that the inhibitory action of the enzyme is caused by the depletion/removal of circulatory L-asparagine, an essential nutrient to proliferate and survive for some tumor (leukemic) cells which are compromised in L-asparagine synthesis ability, but not for the normal cells. The administration of L-asparaginase into leukemic patients induces the selective death of the tumor cells by hydrolyzing L-asparagine, resulting in the treatment of malignant tumors.

L-asparaginase was purified and characterized from several sources, bacteria, (*Escherichia coli*, *Erwinia carotovora*), plants (*Withania somnifera*), fungi, (*Aspergillus niger, A. oryzae*) etc. Among mammals, L-asparaginase is found in more than trace amounts only in Guinea pigs (superfamily Cavioidea) and in certain New World monkeys. Of these L-asparaginases from *E. coli* and *Er. chrysanthemi* are commercially available for the treatment of leukemia. *E. coli* L-asparaginase II (also known as L-asparagine amidohydrolase, type EC-2, EC 3.5.1.1) is commercially available as Elspar® (Merck & Co., Inc.) and is also available from Kyowa Hakko Kogyo Co., Ltd.

The available asparaginases with potent anti-leukemic activity, upon administration to the patients resulted in a wide range of host toxicity (e.g., hepatic, renal, splenic, pancreatic dysfunction and blood coagulation) and pronounced immuno-suppression (Ohno, R. & Hersh, E. M, *Immunosuppressive effects of L-asparaginase,* 30 Cancer Res. 1605 (1970)). Another effect of *E. coli* asparaginase treatment on spleen and lymphocyte was found as a marked reduction in both the size and reactivity of the splenic germinal centers concomitant with a reduction in lymphocyte population (Distasio, J. A., et al., *Alteration in spleen lymphoid populations associated with specific amino acid depletion during L-asparaginase treatment,* 42 Cancer Res. 252 (1982)). Hepatic dysfunction is another important adverse clinical effect associated with traditional microbial asparaginase treatment (Schein, P. S., et al., *The toxicity of E. coli asparaginase,* 29 Cancer Res. 426 (1969)). The indications of asparaginase-induced hepatic dysfunction and pathology include decreased plasma levels of albumin, anti-thrombin III, cholesterol, phospholipids, and triglycerides and fatty degenerative changes, delayed bromo-sulfophthalein clearance, and increased levels of serum glutamic-oxaloacetic transaminase and alkaline phosphatase. A marked decreased in spleen lymphocytic cells of the B-cell lineage and hepatotoxic effects of currently available asparaginases may be a result of depletion of both asparagine and glutamine hydrolysed by asparaginase. *E. coli* asparaginase has been shown to possess a 2% of glutaminase activity resulting in the observed glutamine deprivation and asparaginase-induced clinical toxicity (Spiers, A. D. S., et al., *L-glutaminase/L-asparaginase: human pharmacology, toxicology, and activity in acute leukemia,* 63 Cancer Treat. Rep. 1019 (1979)).

Another significant problem associated with the use of microbial asparaginases is that patients treated with *E. coli* and *Er. carotovora* asparaginases frequently develop neutralizing antibodies of the IgG and IgM immunoglobulin class (e.g., Cheung, N. & Chau, K., Antibody response to *Escherichia coli* L-asparaginase: Prognostic significance and clinical utility of antibody measurement, 8 Am. J. Pediatric Hematol. Oncol. 99 (1986); Howard, J. B. & Carpenter, F. H. (1972) supra), which allows an immediate rebound of serum levels of asparagine and glutamine. In an attempt to mitigate both the toxic effects and immunosensitivity associated with the therapeutic utilization of *E. coli* and *Er. carotovora* asparaginase, a covalently-modified *E. coli* asparaginase (PEG-asparaginase) was initially developed for use in patients who have developed a delayed-type hypersensitivity to preparations "native" of *E. coli* asparaginase (see Gao, S. & Zhao, G., Chemical modification of enzyme molecules to improve their characteristics, 613 Ann. NY Acad. Sci. 460 (1990)). However, subsequent studies established that the initial development of an immune response against *E. coli* asparaginase resulted in an 80% cross-reactivity against the PEG-asparaginase with concomitant adverse pharmacokinetic effects-neutralization of PEG-asparaginase activity and normalization of the plasma levels of L-asparagine and L-glutamine (see Avramis, V. & Periclou, I., Pharmacodynamic studies of PEG-asparaginase (PEG-ASNase) in pediatric ALL leukemia patients, Seventh International Congress on Anti-Cancer Treatment, Paris, France (1997)). The development of antibodies directed against *E. coli* asparaginase and the modified PEG-asparaginase in patients is associated with neutralization of the enzymatic activity of both the *E. coli* and PEG-asparaginases in vivo, thus potentially resulting in an adverse clinical prognosis.

Beside these, the available enzymes are unstable, having reduced half life requiring multiple dose administration, and require low storage temperature (~2-8° C.). All these factors add to an increase in production cost and results in higher treatment cost.

For making enzyme more thermostable and specific to substrate, protein engineering attempts have been made on the available L-asparaginases (Li, L Z. et al, Enhancing the thermo-stability of *Escherichia coli* L-asparaginase II by substitution with pro in predicted hydrogen-bonded turn structures, Enzyme and Microbial Technology, 41 523-527 (2007), Derst C et al, Engineering the substrate specificity of *Escherichia coli* asparaginase II. Selective reduction of glutaminase activity by amino acid replacements at position 248, Protein Sci. 9 (10) 2009-17, (2000)). A reverse approach to make a thermostable L-asparaginase active at mesophilic conditions has not been attempted so far.

The present invention has been carried out in order to provide asparaginase mutants obtained from *Pyrococcus furiosus* which are stable in nature and are devoid in the drawbacks as enumerated above.

DEFINITION OF TERMS

Mutants: A mutant of a protein e.g., asparaginase, refers to a polypeptide which differs in some way from its form(s) found naturally. For example, a mutant of L-asparaginase will refer to an enzyme wherein one or more amino acids has been modified, deleted or inserted from the naturally occurring amino acid sequence.

Expression vector: Expression vector refers to a nucleic acid, typically a plasmid, into which genes of interest may be cloned and subsequently a protein product may be expressed.
Nomenclature of Amino Acid:

The specification and claims refer to amino acids by their one-letter codes. A particular amino acid in a sequence is identified by its one-letter code and its position, e.g. V1 indicates Val (valine) at position 1, i.e. at the N-terminal.

The nomenclature used herein for defining substitutions is basically used as given in example. K274E indicates substitution of K (Lys) at position 274 with E (Glu). The "/" sign in between substitutions e.g. T53Q/K274E means "and" i.e. that these two individual substitutions are combined in one and the same asparaginase.

BRIEF DESCRIPTION OF THE DRAWINGS AND TABLES

FIG. 1. Agarose gel electrophoresis of 981 bp fragment derived from PCR amplification [lane2, 3, 4] using *P. furiosus* L-asparaginase specific two PCR primers as shown in FIG. 1, Lane 1 is 100 bp DNA ladder.

Figure 2:
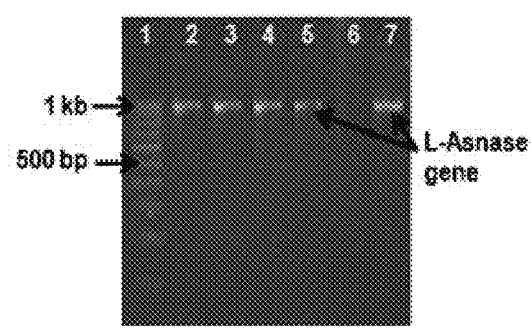

FIG. 2. Agarose gel electrophoresis of the DNA fragment amplified from the randomly selected transformants utilizing *P. furiosus* asparaginase-specific primers. Lane 1 is 100 bp DNA ladders. Lane 7 is a positive control (*P. furiosus* asparaginase PCR amplification product). Lanes 2-6 are the PCR amplified from randomly selected 5 bacterial colonies.

Figure 3:
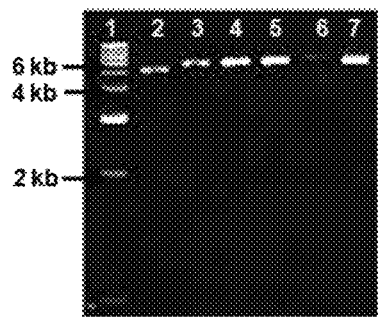

FIG. 3. Restriction enzyme analysis of 5 randomly selected colonies which were isolated following the ligation of the 981 bp *P. furiosus*—specific PCR amplified fragment into the vector. Lane 1 is 1 kb DNA ladder, Lane 2. Control plasmid vector 14b with an insert of 400 bp was digested with BamHI, Lane 3-7 possible recombinant constructs were digested with BamHI.

Figure 4:
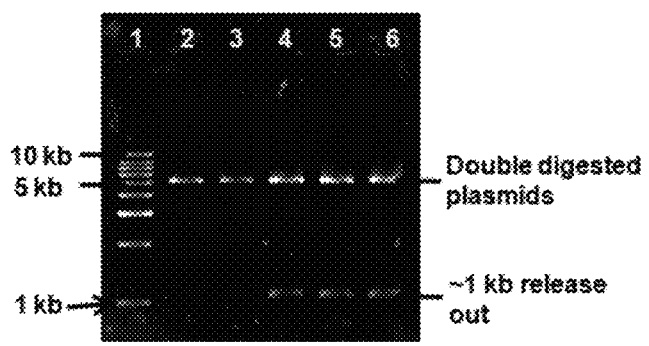

FIG. 4. Restriction enzyme analysis of 4 randomly selected colonies which were isolated following the ligation of the 981 bp *P. furiosus*-specific PCR amplified fragment into the vector. Lane 1 is 1 kb DNA ladder, Lane 2: Control plasmid vector 14b carrying an insert of 400 bp was digested with BamHI and NdeI, Lanes 3-6: possible positive recombinant constructs were digested with BamHI and NdeI. The 981 bp long *P. furiosus* specific DNA fragment is dropped out and denoted by an arrow here.

Figure 5:
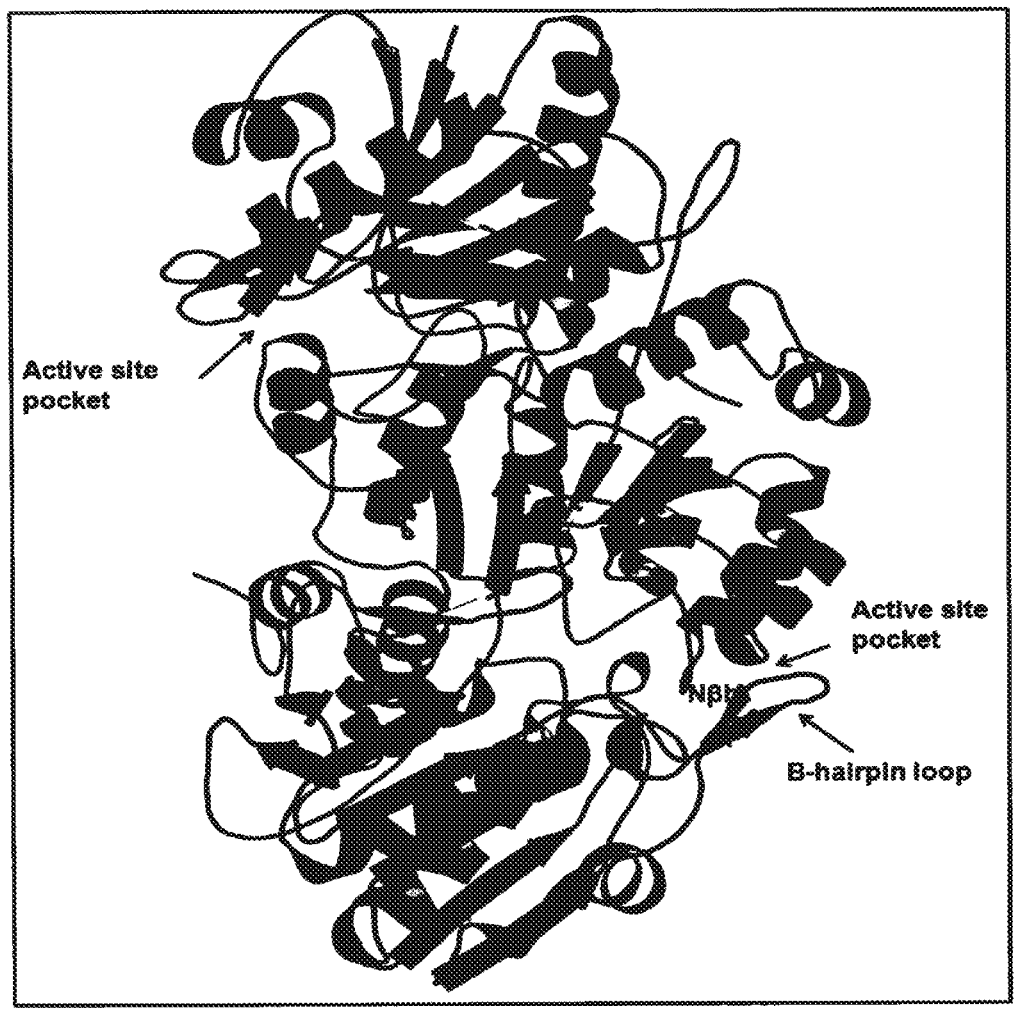

FIG. 5. Shows the 3-dimensional homology modeled structure of *Pyrococcus furiosus* asparaginase.

Figure 6:
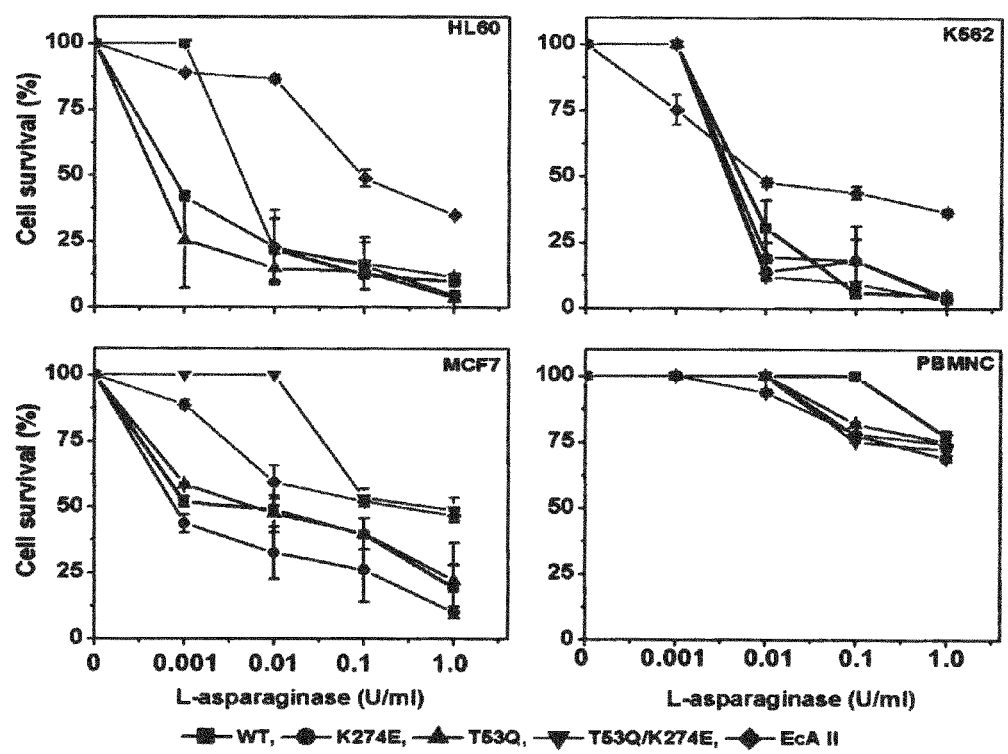

FIG. 6. shows the anti-tumor activity of *P. furiosus* and its three mutants, *E. coli* asparaginases on the cell lines MCF7, K562 and HL-60. Here the cells without treating with asparaginase were taken as positive control.

Table 1. Illustrates the biochemical characteristics of the enzymes at different parameters.

Table. 2. Illustrates the stability parameters of the enzymes.

OBJECT OF THE INVENTION

The principal object of the present invention is to provide mutant of L-asparaginase characterized in having high stability and no glutaminase activity. A thermostable L-asparaginase from *P. furiosus* was cloned and expressed in *E. coli* host. The enzyme was engineered at its active site to create three different mutants based on structural and sequence analysis with a *E. coli*-derived enzyme homologue. The mutants MTCC 5580, MTCC 5581 and MTCC 5582 were tested for their stability, substrate affinity, optimum pH and temperature of activity and cytotoxicity. Based on the studies, all the three enzymes were found thermostable and with no glutaminase activity as compared to other available enzyme EcA II. MTCC 5579 and the above said three mutants showed the cytotoxicity on the leukemic cell lines. The present study showed that these enzymes are promising candidates for the treatment of leukemia.

Another object of the invention is to provide a process for preparing mutants of L-asparaginase.

Yet another object of the present invention is to provide primers selected from the group comprising of Seq Id no. 12, 13, 14, 15, 16, 17, useful for the amplification of wild type and mutant L-asparaginase gene.

Yet another object of the present invention is to provide novel expression constructs for L-asparaginase enzyme.

Yet another object of the present invention is to provide novel Recombinant *E. coli* strains having accession number, MTCC 5579, MTCC 5580, MTCC 5581 and MTCC 5582.

Yet another object of the present invention is to provide method of treatment for Leukemia and asparagine depletion related disorders using mutants of L-asparaginases.

Still another object of the present invention is to provide a formulation administered intramuscularly (IM) and intravenously (IV).

Yet another object of the present invention is to provide use of mutants of L-asparaginase in acrylamide reduction in food products.

Yet another object of the present invention is to provide a method for reducing the production of acrylamide during the processing of food.

SUMMARY OF THE INVENTION

Accordingly, the present invention provides novel mutants of L-asparaginase from *Pyrococcus furiosus*. Based on structural and functional considerations, asparaginase mutants were constructed having modified amino acid residues at the identified positions and having altered physiochemical properties, especially improved relative activity at high and low temperatures. The present invention involves method of preparing recombinant asparaginase MTCC 5579, and its mutants MTCC 5580, MTCC 5581, and MTCC 5582 characterized in having higher stability and no glutaminase activity useful for the treatment of leukemia and other diseases where asparagine depletion or deprivation would be efficacious.

The present invention also relates to isolated nucleic acid sequences encoding the asparaginases and to nucleic acid constructs, expression vectors, and host cells comprising the nucleic acid sequences as well as methods for producing and using the asparaginases.

DETAILED DESCRIPTION OF THE INVENTION

The aim of the present invention is to eradicate the foregoing problems through the provision of a therapeutically effective and immunologically-distinct, alternative and stable form of asparaginase, i.e., *P. furiosus* asparaginase (PfA) or their mutants thereof. These asparaginases and their process for preparation are described in detail below, enable them to be used for treating patients suffering from diseases, such patients responding to asparagine deprivation as first line therapy or, alternatively, for treating patients who had previously developed hyper-sensitization to other microbial asparaginases, e.g., that derived from *E. coli*, and/or modified forms of non-*P. furiosus* asparaginases, e.g., *E. coli* or *Er. carotovora* asparaginase that has been PEGylated.

The Applicants have modeled the three-dimensional structure of an asparaginase from *P. furiosus* based on the published structure of a homologous enzyme from *P. horikoshii*. Based on the modeled structure and sequence alignment analysis with that of *E. coli*, the inventors have identified amino acid residues of relevance for improving the properties of the asparaginase.

The recombinant enzymes of the present invention, are stable in nature, as a result of which, they may also be used in the production of food products where it can be used to prevent the acrylamide synthesis.

It is pertinent to mention that available enzymes had various drawbacks which ranged from instability to causing milder as well as severe side effects. It was also found that the side effects caused by the available enzymes were reportedly associated with glutaminase activity.

In stark contrast, the L-asparaginases of the present invention have manifold advantages; such enzymes being are devoid of any glutaminase activity. As a result, certain undesired side effects which were caused by existing and available enzymatic treatments are anticipated to be either greatly mitigated or non-existent on treatment with L-asparaginases of the present invention. Therefore, the enzymes of the present invention provide the means of an alternative therapeutical method for the treatment of leukemia and likewise diseases where asparagine depletion or deprivation would be efficacious.

Other significant advantages of the present invention are that the aforesaid enzymes being stable enzymes which reduce the treatment cost through its long half life in serum; resulting in reducing the need of multiple dose administration to the patients.

Further, an important aspect of the present invention is to reduce the production cost of the enzymes due to milder temperature requirements during production of L-asparaginases of the present invention. Another important feature of the invention is that the L-asparaginase of the present invention does not require any sophisticated storage condition.

The present invention also provides the stable enzymes for food industry as acrylamide synthesis inhibitor.

A principal embodiment of the present invention is a novel mutant of L-asparaginase enzyme characterized in having high thermostability, pH stability and no glutaminase activity useful for therapeutics.

Yet another embodiment of the present invention is the mutant of L-asparaginase enzyme wherein high thermostability is in the temperature range of 37-90° C.

Yet another embodiment of the present invention is the mutant of L-asparaginase enzyme wherein the pH stability is in the range of 7.0-9.5.

Yet another embodiment of the present invention is the mutant of L-asparaginase enzyme wherein the polypeptide sequence of the enzyme is selected from the group consisting of Seq. ID No. 6, 8, 10.

Yet another embodiment of the present invention is the polypeptide sequence comprising at least one of the following substitutions K274E, T53Q, and T53Q/K274E.

Yet another embodiment of the present invention is the nucleic acid sequence corresponding to the polypeptide sequence is selected from the group consisting of SEQ ID No 7, 9, 11.

Yet another embodiment of the present invention is the primer sequence selected from the group consisting of Seq ID No. 14, 15, 16, and 17, useful for the amplification of mutant L-asparaginase gene.

Yet another embodiment of the present invention is an expression construct comprising any one of the modified nucleic acids.

Yet another embodiment of the present invention is a host cell comprising the expression construct.

In Yet another embodiment of the present invention a recombinant *E. coli* strain having the construct having International Deposition No. MTCC 5579, 5580, 5581 and 5582 in the International Depository "Microbial Type Culture Collection" at Institute of Microbial Technology, Chandigarh, India.

Further in another embodiment the invention provides a process of preparing the mutant L-asparaginase wherein it comprises the steps of:

isolating *Pyrococcus furiosus* asparaginase gene having Seq Id no. 2;

amplifying the gene obtained in step a, using primers having Seq Id. No. 12 and 13.

cloning the gene obtained in step b, in an expression construct.

mutagenizing the gene in the recombinant construct obtained in step c, using site directed mutagenesis, transforming the expression construct obtained in step d, into *E. coli*, purifying the mutant L-asparaginase enzyme.

In yet another embodiment the present invention provides a pharmaceutical composition comprising the L-asparaginase mutant, optionally along with pharmaceutically acceptable excipient(s).

In yet another embodiment the present invention provides a pharmaceutical composition for treating disease or disorder selected from the group consisting of Leukemia and asparagine depletion related disorders.

In yet another embodiment the present invention provides a pharmaceutical composition administered intramuscularly (IM) and intravenously (IV).

In yet another embodiment the present invention provides the use of mutant of L-Asparaginase in acrylamide reduction in food products.

In yet another embodiment the present invention provides a use of L-asparaginase as medicament in the treatment of a cancer.

Further in another embodiment the invention provides an isolated L-asparaginase enzyme of *Pyrococcus furiosus* having Seq ID no. 4.

In yet another embodiment the invention provides the isolated polypeptide sequence of the L-asparaginase enzyme having Sequence ID no. 1.

In yet another embodiment the invention provides the isolated corresponding nucleic acid of the polypeptide sequence having Seq. ID 2.

In yet another embodiment the invention provides the method of isolating L-asparaginase enzyme of *Pyrococcus furiosus* comprising the steps of:
- isolating *Pyrococcus furiosus* asparaginase gene having Seq Id no. 2;
- amplifying the gene obtained in step a, using primers having Seq Id. No. 12 and 13.
- cloning the gene obtained in step b, in an expression construct.
- transforming the expression construct obtained in step d, into *E. coli*,
- purifying the L-asparaginase enzyme having Seq Id no. 3 using Ni-NTA resins.
- removing His-tag by thrombin cleavage from the enzyme obtained in step e as herein described,
- purifying the L-asparaginase without his-tag obtained in step f having Seq Id no. 4.

In yet another embodiment the invention provides the modeled structure of the L-asparaginase enzyme of *Pyrococcus furiosus* having Seq ID No. 3.

The following examples are given by way of illustration of the present invention and therefore should not be construed to limit the scope of the present invention.

WORKING EXAMPLES

Example 1

PCR Amplification of *P. furiosus* Asparaginase Sequences

The nucleotide sequence of 981 bp coding region of *P. furiosus* asparaginase (Seq ID: 2) is obtained from GeneBank accession number (NC_003413.1). From the sequence, the specific primers (Seq ID: 12, 13) for the PCR amplification of the gene coding *P. furiosus* asparaginase is synthesized.

PCR amplification using these primers (FIG. 1) introduced an NdeI and a BamHI restriction site to the 5' and 3' termini of the nucleotide sequences, respectively to facilitate directional cloning of this amplified genomic sequence into sequencing and/or expression vectors.

Example 2

Cloning of *P. furiosus* Asparaginase Sequences

The amplified *P. furiosus* asparaginase-specific amplified DNA fragment is double digested with NdeI and BamHI and cloned into the NdeI and BamHI sites of the double digested pET 14b vector (Novagen, USA) utilizing the specific conditions. The ligation reaction is incubated at 16° C. for 16 hr. and then 2 μl of this reaction is used to transform competent *E. coli* strain DH5α. Transformants are then plated onto LA plates containing 100 μg/ml ampicillin and incubated at 37° C., for 14 hr.

Randomly 5 colonies are selected out from the LA plate. These colonies are then grown in LB media containing 100 μg/ml ampicillin by incubating overnight at 37° C. on a shaker. From these cultures, plasmids are isolated using a standard DNA "mini-prep" methodology. The concentration of plasmids was determined using spectrometric method at 260 nm. Then the plasmids are single and double digested with NdeI and BamHI restriction enzymes and run over the agarose gel along with a control plasmid without having insert as illustrated in FIG. 3. For the confirmation of the result, the *P. furiosus* asparaginase specific PCR primers are used to amplify the *P. furiosus* asparaginase-specific fragments isolated from the earlier mentioned clones (FIG. 4). These primers did not mediate amplification of non-insert containing bacterial DNA. The final confirmation of the clone is done by DNA sequencing.

Example 3

Homology Modeling

In the absence of the structure of PfA, a homology model of the same is constructed using MODELLER (Sali & Blundell, 1993). The available crystal structure of *P. horikoshii* L-asparaginase (PhA; PDB: 1 WLS) is used as template. The sequence alignment module in MODELLER is used to prepare the alignment files of the target and the template. These alignment files are further used to generate the 3D-structure model. Ramachandran plots for the model and template L-asparaginases has been analyzed for verifying the quality of the model (Kleywegt & Jones, 1996).

Example 4

Site Directed Mutagenesis for Creating Different Mutants of *P. furiosus* Asparaginase Two synthetic oligonucleotide primers (complementary to each other) containing the desired mutation is used to amplify (PCR) the entire vector containing an insert of interest. The product obtained is treated with DpnI to digest the parental DNA template (semi-methylated) and to select for mutation-containing synthesized DNA (non-methylated). The nicked vector DNA containing the desired mutations is then transformed into *E. coli* strain DH5α-competent cells (FIG. 7a-7c). Mutation was confirmed by DNA sequencing. For creating three different mutants, 2 set of primers (Seq ID: 14, 15, 16 and 17) are used.

The primers used for generating second site directed mutant T53Q are used to make another site directed mutant (a double mutant) through PCR over K274E mutant plasmid as a template or vice-versa.

Example 5

Expression of Recombinant *P. furiosus* Asparaginase and its Mutants

The enzyme is expressed in *E. coli* strains, BL21CODON PLUS (Invitrogen) and/or Rosetta (Novagen). To facilitate the purification of the enzyme, poly-His tag at N-terminal of the recombinant asparaginase is kept.

Nickel resin (Ni-NTA [nitilo-tri-acetic acid resin]; Qiagen) is used to affinity purify the poly-His labeled recombinant asparaginase enzyme. The Poly-His tag is cleaved by thrombin which leaves three extra amino acids (GSH) at the N-terminus of L-asparaginases.

Example 6

Purification of L-Asparaginase and its Mutants

The enzyme is purified under denature conditions according to the following methodology. Clone strains are grown to ~0.6 $OD_{600nm}$, in the presence of chloramphenicol (17 µg/ml) and ampicillin (100 µg/ml) at 37° C. with shaking and then induced with IPTG (1 mM). Then the cells are harvested by centrifugation and cell pellet obtained is lysed by sonication in lysis buffer [100 mM $NaH_2PO_4$, 10 mM Tris-Cl, 6 M Guanidine Chloride (GdnCl)/8 M Urea (pH 8.0)]. Following centrifugation, the supernatant is filtered with 0.45 µm filters. The filtrate is then incubated with Ni-NTA agarose resins, which is packed in a column for purification. After washing with wash buffer (pH 6.3), protein is eluted in elution buffer (pH 5.9, 4.5). Eluted fractions were collected in aliquots of 1 ml and analyzed on 12% SDS-PAGE. After analysis, the fraction containing the protein of interest is pooled followed by dialysis against 50 mM Tris-Cl, 100 mM NaCl, pH 8.0. Dialysed protein sample is then centrifuged to remove any precipitated protein fraction and then stored at 4° C.

Example 7

Biochemical Characterization of Asparaginase

The enzymes is characterized in the terms of $K_m$, $V_{max}$, catalytic efficiency, enzyme kinetics (Table 1), substrate specificity, pH optimum, and temperature optimum. SDS-PAGE followed by Coomassie Blue staining of the gels, is used to observe enzyme homogeneity, evaluate subunit composition and determine enzyme molecular weight. Gel filtration chromatography was carried out to determine its multimericity.

TABLE 1

| L-asparaginase | 80° C., pH 8.2 | | | | 37° C., pH 7.4 | | | |
|---|---|---|---|---|---|---|---|---|
| | $K_m \times 10^{-3}$ (M) | $K_{cat}$ ($sec^{-1}$) | $K_{cat}/K_m$ ($M^{-1}sec^{-1}$) | Ks (M) | $K_m \times 10^{-3}$ (M) | $K_{cat}$ ($sec^{-1}$) | $K_{cat}/K_m$ ($M^{-1}sec^{-1}$) | Ks (mM) |
| MTCC 5579 | 12.1 ± 0.05 | 889 ± 54 | 73000 | 125 ± 50 | 8.1 ± 0.3 | 18 ± 0.6 | 2210 | — |
| MTCC 5580 | 2.1 ± 0.04 | 199 ± 2 | 96000 | 440 ± 100 | 4.3 ± 0.3 | 25 ± 0.97 | 5780 | 160 ± 30 |
| MTCC 5581 | 8.3 ± 1.0 | 247 ± 14 | 30000 | 100 ± 20 | 7.5 ± 1.0 | 35 ± 1.9 | 4720 | 110 ± 20 |
| MTCC 5582 | 8.2 ± 1.4 | 278 ± 27 | 34000 | 120 ± 40 | 5.4 ± 0.3 | 24 ± 0.6 | 4400 | 220 ± 40 |

Enzymatic activity of L-asparaginase is quantitatively measured by the amount of ammonia released upon hydrolysis of L-asparagine using 50 mM buffer at pH 7.4 and 9.0. In short, reaction mixture containing 50 mM Tris-HCl pH 9.0, or 50 mM Na-phosphate, pH 7.4, 10 mM L-asparagine (Merck) and varying amount of enzyme solution in a final volume of 2 ml is incubated for 10 minutes at 80° C., or 37° C. After incubation the reaction is stopped by adding 100 µl of 1.5 M trichloroacetic acid (TCA). The solution is centrifuged followed by addition of 1 ml Nessler's reagent (Merck) to 500 µl of the supernatant diluted with 7 ml water. $OD_{480nm}$ of the resulting solution gave a measure of enzyme activity. A standard curve is prepared with ammonium sulphate. One international unit (IU) of L-asparaginase activity is defined as the amount of enzyme liberating 1 µmol $NH_3$ in one minute incubated at the above mentioned conditions. Specific activity of L-asparaginase is defined as the units per milligram protein.

Example 8

Stability Determination of Asparaginase

Enzyme stability is determined by incubating the enzyme with varying concentration of GdnCl (Table 2), Urea, increasing temperature and varying pH for various time intervals.

| Enzyme | $\Delta G(H_2O)$ (Kcal/mol) | Mid-point melting transition with GdnCl (Cm) (M) | m (kcal/mol/M) |
|---|---|---|---|
| MTCC 5579 | 8.6 ± 0.8 | 3.56 | 2.41 ± 0.24 |
| MTCC 5580 | 8.0 ± 0.4 | 3.58 | 2.24 ± 0.11 |

-continued

| Enzyme | ΔG(H₂O) (Kcal/mol) | Mid-point melting transition with GdnCl (Cm) (M) | m (kcal/mol/M) |
|---|---|---|---|
| MTCC 5581 | 11.4 ± 0.8 | 3.6 | 3.16 ± 0.22 |
| MTCC 5582 | 7.5 ± 0.9 | 3.49 | 2.15 ± 0.27 |

Example 9

Determination of the Cyto-Toxicity (Anti-Neoplastic) Activity of Asparaginase

The cell lines are grown in RPMI-1640 medium containing 10% FCS in the presence of 100 IU/ml penicillin and 100 μg/ml streptomycin, in 5% $CO_2$ incubator at 37° C. The control culture is treated with regular media only. MTT colorimetry is employed to investigate the proliferation of cells. Cells (K562, HL-60 and MCF7) at the logarithmic growth phase are suspended in solution to a cell density $2.5 \times 10^4$/ml. This suspension (100 μl per well) is then transferred to each well. The varying concentration (0.001, 0.01, 0.1 and 1.0 IU/ml) of enzymes are added to the cell lines and the volume is made up to 200 μl with RPMI 1640 culture media. The plate is incubated in 5% $CO_2$ incubator at 37° C. for varying time (24, 48, 72 hr.) After each time periods, the 20 μl of 5 mg/ml MTT is added in each well and then further incubated for 2 hr. in the same incubator. Cells are then isolated by centrifugation and cell pellets are suspended in 150 μl DMSO followed by 30 min. incubation. Absorbance is measured at 540 nm after cells are completely dissolved.

ADVANTAGES OF THE PRESENT INVENTION

The enzyme disclosed in the present invention is devoid of any glutaminase activity thereby reducing undesired side effects caused by existing and available enzymatic treatments.

The present invention provides a useful alternative therapeutic method for treatment of leukemia and likewise diseases where L-asparagines depletion or deprivation would be efficacious.

The enzymes claimed in the invention are thermally stable and have long shelf-lives which reduce storage costs.

Being stable the enzymes of this invention have long half life in serum in treated patients resulting in reduction in dose requirement for treatment.

The present invention provides an enzyme which is easy to produce and purify in quantities thereby reducing the cost of treatment.

The present invention also provides stable enzymes that can be used in food industry for reduction of toxic acrylamide in fried and baked foods.

We claim:

1. A mutant of L-asparaginase comprising an amino acid sequence selected from the group consisting of SEQ ID NO: 8 and SEQ ID NO: 10.

2. The mutant of L-asparaginase of claim 1, wherein said mutant is stable in the temperature range of 37-90° C.

3. The mutant of L-asparaginase of claim 1, wherein said mutant is stable in the pH range of 7.0-9.5.

4. The mutant of L-asparaginase of claim 1, wherein said mutant has no glutaminase activity.

5. The mutant of L-asparaginase of claim 1, which is encoded by a polynucleotide comprising a sequence amplified by primer sequences selected from the group consisting of SEQ ID NO: 14, SEQ ID NO: 15, SEQ ID NO: 16, and SEQ ID NO: 17.

6. A composition comprising the L-asparaginase mutant of claim 1 and a pharmaceutically acceptable excipient.

7. A polynucleotide encoding the mutant of L-asparaginase of claim 1, said polynucleotide comprising a sequence selected from the group consisting of SEQ ID NO: 9 and SEQ ID NO: 11.

8. An expression construct comprising a polynucleotide sequence selected from the group consisting of SEQ ID NO: 9 and SEQ ID NO: 11.

9. A host cell comprising the expression construct of claim 8.

10. A recombinant *E. coli* strain deposited in Microbial Type Culture Collection at Institute of Microbial Technology, India, said *E. coli* strain having International Deposition No. MTCC 5581 or MTCC 5582.

11. A method of preparing the mutant L-asparaginase of claim 1, comprising:
(a) isolating a *Pyrococcus furiosus* asparaginase gene comprising the polynucleotide sequence of SEQ ID NO: 2, using a pair of primers having the polynucleotide sequences of SEQ ID NO: 12 and SEQ ID NO: 13, respectively;
(b) cloning the gene isolated in step (a), into an expression construct;
(c) mutagenizing the gene in the expression construct obtained in step (b), using site directed mutagenesis;
(d) transforming the expression construct obtained in step (c), into *E. coli*; and
(e) purifying the mutant L-asparaginase from the *E. coli* of step (d).

12. A method of treating a cancer in a subject in need thereof, comprising administering to the subject the composition of claim 6, thereby treating the cancer.

13. The method of claim 12, wherein the composition is administered intramuscularly (IM) or intravenously (IV) to the subject.

14. The method of claim 12, wherein the cancer is leukemia.

15. A method of reducing acrylamide levels in a food product, comprising introducing into said food product the L-asparaginase mutant of claim 1.

* * * * *

SEQUENCE LISTING

<160> NUMBER OF SEQ ID NOS: 17

<210> SEQ ID NO 1
<211> LENGTH: 326
<212> TYPE: PRT
<213> ORGANISM: P.furiosus

<400> SEQUENCE: 1

Met Lys Ile Leu Leu Ile Gly Met Gly Gly Thr Ile Ala Ser Val Lys
1               5                   10                  15

Gly Glu Asn Gly Tyr Glu Ala Ser Leu Ser Val Lys Glu Val Leu Asp
            20                  25                  30

Ile Ala Gly Ile Lys Asp Cys Glu Asp Cys Asp Phe Leu Asp Leu Lys
        35                  40                  45

Asn Val Asp Ser Thr Leu Ile Gln Pro Glu Asp Trp Val Asp Leu Ala
    50                  55                  60

Glu Thr Leu Tyr Lys Asn Val Lys Lys Tyr Asp Gly Ile Ile Val Thr
65                  70                  75                  80

His Gly Thr Asp Thr Leu Ala Tyr Thr Ser Ser Met Ile Ser Phe Met
                85                  90                  95

Leu Arg Asn Pro Pro Ile Pro Ile Val Phe Thr Gly Ser Met Ile Pro
            100                 105                 110

Ala Thr Glu Glu Asn Ser Asp Ala Pro Leu Asn Leu Gln Thr Ala Ile
        115                 120                 125

Lys Phe Ala Thr Ser Gly Ile Arg Gly Val Tyr Val Ala Phe Asn Gly
    130                 135                 140

Lys Val Met Leu Gly Val Arg Thr Ser Lys Val Arg Thr Met Ser Arg
145                 150                 155                 160

Asp Ala Phe Glu Ser Ile Asn Tyr Pro Ile Ile Ala Glu Leu Arg Gly
                165                 170                 175

Glu Asp Leu Val Val Asn Phe Ile Pro Lys Phe Asn Asn Gly Glu Val

```
                   180                 185                 190
Thr Leu Asp Leu Arg His Asp Pro Lys Val Leu Val Ile Lys Leu Ile
            195                 200                 205
Pro Gly Leu Ser Gly Asp Ile Phe Arg Ala Ala Val Glu Leu Gly Tyr
        210                 215                 220
Arg Gly Ile Val Ile Glu Gly Tyr Gly Ala Gly Ile Pro Tyr Arg
225                 230                 235                 240
Gly Ser Asp Leu Leu Gln Thr Ile Glu Glu Leu Ser Lys Glu Ile Pro
                245                 250                 255
Ile Val Met Thr Thr Gln Ala Met Tyr Asp Gly Val Asp Leu Thr Arg
            260                 265                 270
Tyr Lys Val Gly Arg Leu Ala Leu Arg Ala Gly Val Ile Pro Ala Gly
        275                 280                 285
Asp Met Thr Lys Glu Ala Thr Val Thr Lys Leu Met Trp Ile Leu Gly
            290                 295                 300
His Thr Asn Asn Val Glu Glu Ile Lys Val Leu Met Arg Lys Asn Leu
305                 310                 315                 320
Val Gly Glu Leu Arg Asp
                325
```

<210> SEQ ID NO 2
<211> LENGTH: 981
<212> TYPE: DNA
<213> ORGANISM: p.furiosus

<400> SEQUENCE: 2

```
gtgaaaattc ttctaattgg gatgggtgga acaattgcga gtgtaaaggg cgagaatgga      60
tatgaggctt cgttgtccgt taaagaagtt ttagatatcg ccggaatcaa agattgtgag     120
gattgtgatt ttctcgattt aaagaacgtt gatagcacgc ttatccagcc agaagattgg     180
gtagatcttg ctgaaactct ttacaagaat gtaaaaaaat atgatggaat tatagtcact     240
catggtaccg atactcttgc ctacacttct tcaatgataa gtttcatgct tagaaacccc     300
ccaatacccca tcgtatttac tggttctatg ataccctgcca ctgaagaaaa tagtgatgcc     360
cccctaaaact tgcaaacagc aataaagttt gcaacttctg gaattagggg agtttacgtg     420
gccttcaatg gaaaagttat gcttggagtt agaacatcta aggttaggac aatgagcaga     480
gatgcattcg aaagcattaa ctaccctata attgcagaat taagaggaga gatctcgtg     540
gttaactta ttccaaagtt taacaatgga gaagtcacat tagaccttag cacgatcca     600
aaagttctag ttataaagct aatcccagga ctttcggggg acatatttag ggcagctgta     660
gagctgggat atagaggaat tgtcatagaa ggttatggag ctggaggaat tccttatagg     720
ggaagtgatt tacttcaaac aatagaggag ctctccaagg agattccaat agtaatgaca     780
acccaggcaa tgtacgatgg agttgatcta acgaggtaca agttgggag attagcccctt     840
agagctggag taatcccagc gggggacatg acaaaagagg caacagtaac aaagctcatg     900
tggattctag gccacacaaa caatgtggaa gaaataaaag tattaatgag aaaaaatcta     960
gttggagagc ttagagatta a                                                981
```

<210> SEQ ID NO 3
<211> LENGTH: 346
<212> TYPE: PRT
<213> ORGANISM: p.furiosus

<400> SEQUENCE: 3

```
Met Gly Ser Ser His His His His His Ser Ser Gly Leu Val Pro
1               5                   10                  15

Arg Gly Ser His Met Lys Ile Leu Leu Ile Gly Met Gly Gly Thr Ile
                20                  25                  30

Ala Ser Val Lys Gly Glu Asn Gly Tyr Glu Ala Ser Leu Ser Val Lys
            35                  40                  45

Glu Val Leu Asp Ile Ala Gly Ile Lys Asp Cys Glu Asp Cys Asp Phe
    50                  55                  60

Leu Asp Leu Lys Asn Val Asp Ser Thr Leu Ile Gln Pro Glu Asp Trp
65                  70                  75                  80

Val Asp Leu Ala Glu Thr Leu Tyr Lys Asn Val Lys Lys Tyr Asp Gly
                85                  90                  95

Ile Ile Val Thr His Gly Thr Asp Thr Leu Ala Tyr Thr Ser Ser Met
            100                 105                 110

Ile Ser Phe Met Leu Arg Asn Pro Pro Ile Pro Ile Val Phe Thr Gly
        115                 120                 125

Ser Met Ile Pro Ala Thr Glu Glu Asn Ser Asp Ala Pro Leu Asn Leu
    130                 135                 140

Gln Thr Ala Ile Lys Phe Ala Thr Ser Gly Ile Arg Gly Val Tyr Val
145                 150                 155                 160

Ala Phe Asn Gly Lys Val Met Leu Gly Val Arg Thr Ser Lys Val Arg
                165                 170                 175

Thr Met Ser Arg Asp Ala Phe Glu Ser Ile Asn Tyr Pro Ile Ile Ala
            180                 185                 190

Glu Leu Arg Gly Glu Asp Leu Val Val Asn Phe Ile Pro Lys Phe Asn
        195                 200                 205

Asn Gly Glu Val Thr Leu Asp Leu Arg His Asp Pro Lys Val Leu Val
    210                 215                 220

Ile Lys Leu Ile Pro Gly Leu Ser Gly Asp Ile Phe Arg Ala Ala Val
225                 230                 235                 240

Glu Leu Gly Tyr Arg Gly Ile Val Ile Glu Gly Tyr Gly Ala Gly Gly
                245                 250                 255

Ile Pro Tyr Arg Gly Ser Asp Leu Leu Gln Thr Ile Glu Glu Leu Ser
            260                 265                 270

Lys Glu Ile Pro Ile Val Met Thr Thr Gln Ala Met Tyr Asp Gly Val
        275                 280                 285

Asp Leu Thr Arg Tyr Lys Val Gly Arg Leu Ala Leu Arg Ala Gly Val
    290                 295                 300

Ile Pro Ala Gly Asp Met Thr Lys Glu Ala Thr Val Thr Lys Leu Met
305                 310                 315                 320

Trp Ile Leu Gly His Thr Asn Asn Val Glu Glu Ile Lys Val Leu Met
                325                 330                 335

Arg Lys Asn Leu Val Gly Glu Leu Arg Asp
            340                 345

<210> SEQ ID NO 4
<211> LENGTH: 329
<212> TYPE: PRT
<213> ORGANISM: p.furiosus

<400> SEQUENCE: 4

Gly Ser His Met Lys Ile Leu Leu Ile Gly Met Gly Gly Thr Ile Ala
1               5                   10                  15

Ser Val Lys Gly Glu Asn Gly Tyr Glu Ala Ser Leu Ser Val Lys Glu
                20                  25                  30
```

```
Val Leu Asp Ile Ala Gly Ile Lys Asp Cys Glu Asp Cys Asp Phe Leu
         35                  40                  45

Asp Leu Lys Asn Val Asp Ser Thr Leu Ile Gln Pro Glu Asp Trp Val
 50                  55                  60

Asp Leu Ala Glu Thr Leu Tyr Lys Asn Val Lys Lys Tyr Asp Gly Ile
 65                  70                  75                  80

Ile Val Thr His Gly Thr Asp Thr Leu Ala Tyr Thr Ser Ser Met Ile
                 85                  90                  95

Ser Phe Met Leu Arg Asn Pro Pro Ile Pro Val Phe Thr Gly Ser
             100                 105                 110

Met Ile Pro Ala Thr Glu Glu Asn Ser Asp Ala Pro Leu Asn Leu Gln
             115                 120                 125

Thr Ala Ile Lys Phe Ala Thr Ser Gly Ile Arg Gly Val Tyr Val Ala
 130                 135                 140

Phe Asn Gly Lys Val Met Leu Gly Val Arg Thr Ser Lys Val Arg Thr
145                 150                 155                 160

Met Ser Arg Asp Ala Phe Glu Ser Ile Asn Tyr Pro Ile Ile Ala Glu
                165                 170                 175

Leu Arg Gly Glu Asp Leu Val Val Asn Phe Ile Pro Lys Phe Asn Asn
            180                 185                 190

Gly Glu Val Thr Leu Asp Leu Arg His Asp Pro Lys Val Leu Val Ile
            195                 200                 205

Lys Leu Ile Pro Gly Leu Ser Gly Asp Ile Phe Arg Ala Ala Val Glu
210                 215                 220

Leu Gly Tyr Arg Gly Ile Val Ile Glu Gly Tyr Gly Ala Gly Gly Ile
225                 230                 235                 240

Pro Tyr Arg Gly Ser Asp Leu Leu Gln Thr Ile Glu Glu Leu Ser Lys
                245                 250                 255

Glu Ile Pro Ile Val Met Thr Thr Gln Ala Met Tyr Asp Gly Val Asp
            260                 265                 270

Leu Thr Arg Tyr Lys Val Gly Arg Leu Ala Leu Arg Ala Gly Val Ile
            275                 280                 285

Pro Ala Gly Asp Met Thr Lys Glu Ala Thr Val Thr Lys Leu Met Trp
290                 295                 300

Ile Leu Gly His Thr Asn Asn Val Glu Glu Ile Lys Val Leu Met Arg
305                 310                 315                 320

Lys Asn Leu Val Gly Glu Leu Arg Asp
                325

<210> SEQ ID NO 5
<211> LENGTH: 1041
<212> TYPE: DNA
<213> ORGANISM: p.furiosus

<400> SEQUENCE: 5
atgggcagca gccatcatca tcatcatcac agcagcggcc tggtgccgcg cggcagccat    60
atgaaaattc ttctaattgg gatgggtgga acaattgcga gtgtaaaggg cgagaatgga   120
tatgaggctt cgttgtccgt taaagaagtt ttagatatcg ccggaatcaa agattgtgag   180
gattgtgatt ttctcgattt aaagaacgtt gatagcacgc ttatccagcc agaagattgg   240
gtagatcttg ctgaaactct ttacaagaat gtaaaaaaat atgatggaat tatagtcact   300
catggtaccg atactcttgc ctacacttct tcaatgataa gtttcatgct agaaaccccc   360
ccaatacccg tcgtatttac tggttctatg ataccctgcca ctgaagaaaa tagtgatgcc   420
```

```
cccctaaact tgcaaacagc aataaagttt gcaacttctg gaattagggg agtttacgtg     480
gccttcaatg gaaaagttat gcttggagtt agaacatcta aggttaggac aatgagcaga     540
gatgcattcg aaagcattaa ctaccctata attgcagaat taagaggaga agatctcgtg     600 gttaactttta ttccaaagtt taacaatgga gaagtcacat tagaccttag gcacgatcca     660
aaagttctag ttataaagct aatcccagga ctttcggggg acatatttag ggcagctgta     720
gagctgggat atagaggaat tgtcatagaa ggttatggag ctggaggaat tccttatagg     780
ggaagtgatt tacttcaaac aatagaggag ctctccaagg agattccaat agtaatgaca     840
acccaggcaa tgtacgatgg agttgatcta acgaggtaca aagttgggag attagcccttt     900 agagctggag taatcccagc gggggacatg acaaagagag caacagtaac aaagctcatg     960
tggattctag ccacacaaa caatgtggaa gaaataaaag tattaatgag aaaaaatcta     1020
gttggagagc ttagagatta a                                             1041
```

<210> SEQ ID NO 6
<211> LENGTH: 326
<212> TYPE: PRT
<213> ORGANISM: p.furiosus

<400> SEQUENCE: 6

```
Met Lys Ile Leu Leu Ile Gly Met Gly Gly Thr Ile Ala Ser Val Lys
1               5                   10                  15

Gly Glu Asn Gly Tyr Glu Ala Ser Leu Ser Val Lys Glu Val Leu Asp
                20                  25                  30

Ile Ala Gly Ile Lys Asp Cys Glu Asp Cys Asp Phe Leu Asp Leu Lys
            35                  40                  45

Asn Val Asp Ser Thr Leu Ile Gln Pro Glu Asp Trp Val Asp Leu Ala
        50                  55                  60

Glu Thr Leu Tyr Lys Asn Val Lys Lys Tyr Asp Gly Ile Ile Val Thr
65                  70                  75                  80

His Gly Thr Asp Thr Leu Ala Tyr Thr Ser Ser Met Ile Ser Phe Met
                85                  90                  95

Leu Arg Asn Pro Pro Ile Pro Ile Val Phe Thr Gly Ser Met Ile Pro
                100                 105                 110

Ala Thr Glu Glu Asn Ser Asp Ala Pro Leu Asn Leu Gln Thr Ala Ile
            115                 120                 125

Lys Phe Ala Thr Ser Gly Ile Arg Gly Val Tyr Val Ala Phe Asn Gly
        130                 135                 140

Lys Val Met Leu Gly Val Arg Thr Ser Lys Val Arg Thr Met Ser Arg
145                 150                 155                 160

Asp Ala Phe Glu Ser Ile Asn Tyr Pro Ile Ile Ala Glu Leu Arg Gly
                165                 170                 175

Glu Asp Leu Val Val Asn Phe Ile Pro Lys Phe Asn Asn Gly Glu Val
            180                 185                 190

Thr Leu Asp Leu Arg His Asp Pro Lys Val Leu Val Ile Lys Leu Ile
        195                 200                 205

Pro Gly Leu Ser Gly Asp Ile Phe Arg Ala Ala Val Glu Leu Gly Tyr
    210                 215                 220

Arg Gly Ile Val Ile Glu Gly Tyr Gly Ala Gly Gly Ile Pro Tyr Arg
225                 230                 235                 240

Gly Ser Asp Leu Leu Gln Thr Ile Glu Glu Leu Ser Lys Glu Ile Pro
                245                 250                 255
```

Ile Val Met Thr Thr Gln Ala Met Tyr Asp Gly Val Asp Leu Thr Arg
            260                 265                 270

Tyr Glu Val Gly Arg Leu Ala Leu Arg Ala Gly Val Ile Pro Ala Gly
        275                 280                 285

Asp Met Thr Lys Glu Ala Thr Val Thr Lys Leu Met Trp Ile Leu Gly
    290                 295                 300

His Thr Asn Asn Val Glu Glu Ile Lys Val Leu Met Arg Lys Asn Leu
305                 310                 315                 320

Val Gly Glu Leu Arg Asp
                325

<210> SEQ ID NO 7
<211> LENGTH: 981
<212> TYPE: DNA
<213> ORGANISM: P.furiosus

<400> SEQUENCE: 7
atgaaaattc ttctaattgg gatgggtgga acaattgcga gtgtaaaggg cgagaatgga       60
tatgaggctt cgttgtccgt taagaagtt ttagatatcg ccggaatcaa agattgtgag      120
gattgtgatt ttctcgattt aaagaacgtt gatagcacgc ttatccagcc agaagattgg      180
gtagatcttg ctgaaactct ttacaagaat gtaaaaaaat atgatggaat tatagtcact      240
catggtaccg atactcttgc ctacacttct tcaatgataa gtttcatgct agaaaccccc      300 ccaatacccca tcgtatttac tggttctatg atacctgcca ctgaagaaaa tagtgatgcc      360
cccctaaact tgcaaacagc aataaagttt gcaacttctg gaattagggg agtttacgtg      420
gccttcaatg gaaaagttat gcttggagtt agaacatcta aggttaggac aatgagcaga      480
gatgcattcg aaagcattaa ctaccctata attgcagaat aagaggaga gatctcgtg      540 gttaactttta ttccaaagtt taacaatgga gaagtcacat tagaccttag gcacgatcca      600
aaagttctag ttataaagct aatcccagga ctttcggggg acatatttag ggcagctgta      660
gagctgggat atagaggaat tgtcatagaa ggttatggag ctggaggaat tccttatagg      720
ggaagtgatt tacttcaaac aatagaggag ctctccaagg agattccaat agtaatgaca      780
acccaggcaa tgtacgatgg agttgatcta acgaggtacg aagttgggag attagccctt      840
agagctggag taatcccagc gggggacatg acaaaagagg caacagtaac aaagctcatg      900
tggattctag gccacacaaa caatgtggaa gaaataaaag tattaatgag aaaaaatcta      960
gttggagagc ttagagatta a                                                 981

<210> SEQ ID NO 8
<211> LENGTH: 326
<212> TYPE: PRT
<213> ORGANISM: p.furiosus

<400> SEQUENCE: 8

Met Lys Ile Leu Leu Ile Gly Met Gly Gly Thr Ile Ala Ser Val Lys
1               5                   10                  15

Gly Glu Asn Gly Tyr Glu Ala Ser Leu Ser Val Lys Glu Val Leu Asp
                20                  25                  30

Ile Ala Gly Ile Lys Asp Cys Glu Asp Cys Asp Phe Leu Asp Leu Lys
            35                  40                  45

Asn Val Asp Ser Gln Leu Ile Gln Pro Glu Asp Trp Val Asp Leu Ala
        50                  55                  60

Glu Thr Leu Tyr Lys Asn Val Lys Lys Tyr Asp Gly Ile Ile Val Thr
65                  70                  75                  80

His Gly Thr Asp Thr Leu Ala Tyr Thr Ser Ser Met Ile Ser Phe Met
            85                  90                  95

Leu Arg Asn Pro Pro Ile Pro Ile Val Phe Thr Gly Ser Met Ile Pro
            100                 105                 110

Ala Thr Glu Glu Asn Ser Asp Ala Pro Leu Asn Leu Gln Thr Ala Ile
            115                 120                 125

Lys Phe Ala Thr Ser Gly Ile Arg Gly Val Tyr Val Ala Phe Asn Gly
            130                 135                 140

Lys Val Met Leu Gly Val Arg Thr Ser Lys Val Arg Thr Met Ser Arg
145                 150                 155                 160

Asp Ala Phe Glu Ser Ile Asn Tyr Pro Ile Ile Ala Glu Leu Arg Gly
                165                 170                 175

Glu Asp Leu Val Val Asn Phe Ile Pro Lys Phe Asn Asn Gly Glu Val
            180                 185                 190

Thr Leu Asp Leu Arg His Asp Pro Lys Val Leu Val Ile Lys Leu Ile
            195                 200                 205

Pro Gly Leu Ser Gly Asp Ile Phe Arg Ala Ala Val Glu Leu Gly Tyr
            210                 215                 220

Arg Gly Ile Val Ile Glu Gly Tyr Gly Ala Gly Gly Ile Pro Tyr Arg
225                 230                 235                 240

Gly Ser Asp Leu Leu Gln Thr Ile Glu Glu Leu Ser Lys Glu Ile Pro
                245                 250                 255

Ile Val Met Thr Thr Gln Ala Met Tyr Asp Gly Val Asp Leu Thr Arg
            260                 265                 270

Tyr Lys Val Gly Arg Leu Ala Leu Arg Ala Gly Val Ile Pro Ala Gly
            275                 280                 285

Asp Met Thr Lys Glu Ala Thr Val Thr Lys Leu Met Trp Ile Leu Gly
            290                 295                 300

His Thr Asn Asn Val Glu Glu Ile Lys Val Leu Met Arg Lys Asn Leu
305                 310                 315                 320

Val Gly Glu Leu Arg Asp
                325

<210> SEQ ID NO 9
<211> LENGTH: 981
<212> TYPE: DNA
<213> ORGANISM: P.furiosus

<400> SEQUENCE: 9
atgaaaattc ttctaattgg gatgggtgga acaattgcga gtgtaaaggg cgagaatgga      60
tatgaggctt cgttgtccgt taaagaagtt ttagatatcg ccggaatcaa agattgtgag     120
gattgtgatt ttctcgattt aaagaacgtt gatagccagc ttatccagcc agaagattgg     180
gtagatcttg ctgaaactct ttacaagaat gtaaaaaaat atgatggaat tatagtcact     240
catggtaccg atactcttgc ctacacttct tcaatgataa gtttcatgct agaaaccccc     300
ccaataccca tcgtatttac tggttctatg atacctgcca ctgaagaaaa tagtgatgcc     360
cccctaaact tgcaaacagc aataaagttt gcaacttctg gaattagggg agtttacgtg     420
gccttcaatg gaaagttat gcttggagtt agaacatcta aggttaggac aatgagcaga     480
gatgcattcg aaagcattaa ctaccctata attgcagaat aagaggaga agatctcgtg     540 gttaacttta ttccaaagtt taacaatgga gaagtcacat tagacctag gcacgatcca     600 aaagttctag ttataaagct aatcccagga ctttcggggg acatatttag ggcagctgta     660

```
gagctgggat atagaggaat tgtcatagaa ggttatggag ctggaggaat tccttatagg    720
ggaagtgatt tacttcaaac aatagaggag ctctccaagg agattccaat agtaatgaca    780
acccaggcaa tgtacgatgg agttgatcta acgaggtacg aagttgggag attagccctt    840
agagctggag taatcccagc gggggacatg acaaaagagg caacagtaac aaagctcatg    900
tggattctag gccacacaaa caatgtggaa gaaataaaag tattaatgag aaaaaatcta    960
gttggagagc ttagagatta a                                              981
```

```
<210> SEQ ID NO 10
<211> LENGTH: 326
<212> TYPE: PRT
<213> ORGANISM: p.furiosus

<400> SEQUENCE: 10
```

```
Met Lys Ile Leu Leu Ile Gly Met Gly Gly Thr Ile Ala Ser Val Lys
1               5                   10                  15

Gly Glu Asn Gly Tyr Glu Ala Ser Leu Ser Val Lys Glu Val Leu Asp
            20                  25                  30

Ile Ala Gly Ile Lys Asp Cys Glu Asp Cys Asp Phe Leu Asp Leu Lys
        35                  40                  45

Asn Val Asp Ser Gln Leu Ile Gln Pro Glu Asp Trp Val Asp Leu Ala
    50                  55                  60

Glu Thr Leu Tyr Lys Asn Val Lys Lys Tyr Asp Gly Ile Ile Val Thr
65                  70                  75                  80

His Gly Thr Asp Thr Leu Ala Tyr Thr Ser Ser Met Ile Ser Phe Met
                85                  90                  95

Leu Arg Asn Pro Pro Ile Pro Ile Val Phe Thr Gly Ser Met Ile Pro
            100                 105                 110

Ala Thr Glu Glu Asn Ser Asp Ala Pro Leu Asn Leu Gln Thr Ala Ile
        115                 120                 125

Lys Phe Ala Thr Ser Gly Ile Arg Gly Val Tyr Val Ala Phe Asn Gly
    130                 135                 140

Lys Val Met Leu Gly Val Arg Thr Ser Lys Val Arg Thr Met Ser Arg
145                 150                 155                 160

Asp Ala Phe Glu Ser Ile Asn Tyr Pro Ile Ile Ala Glu Leu Arg Gly
                165                 170                 175

Glu Asp Leu Val Val Asn Phe Ile Pro Lys Phe Asn Asn Gly Glu Val
            180                 185                 190

Thr Leu Asp Leu Arg His Asp Pro Lys Val Leu Val Ile Lys Leu Ile
        195                 200                 205

Pro Gly Leu Ser Gly Asp Ile Phe Arg Ala Ala Val Glu Leu Gly Tyr
    210                 215                 220

Arg Gly Ile Val Ile Glu Gly Tyr Gly Ala Gly Gly Ile Pro Tyr Arg
225                 230                 235                 240

Gly Ser Asp Leu Leu Gln Thr Ile Glu Glu Leu Ser Lys Glu Ile Pro
                245                 250                 255

Ile Val Met Thr Thr Gln Ala Met Tyr Asp Gly Val Asp Leu Thr Arg
            260                 265                 270

Tyr Glu Val Gly Arg Leu Ala Leu Arg Ala Gly Val Ile Pro Ala Gly
        275                 280                 285

Asp Met Thr Lys Glu Ala Thr Val Thr Lys Leu Met Trp Ile Leu Gly
    290                 295                 300

His Thr Asn Asn Val Glu Glu Ile Lys Val Leu Met Arg Lys Asn Leu
305                 310                 315                 320
```

Val Gly Glu Leu Arg Asp
                325

<210> SEQ ID NO 11
<211> LENGTH: 981
<212> TYPE: DNA
<213> ORGANISM: P.furiosus

<400> SEQUENCE: 11

```
atgaaaattc ttctaattgg gatgggtgga acaattgcga gtgtaaaggg cgagaatgga      60
tatgaggctt cgttgtccgt taaagaagtt ttagatatcg ccggaatcaa agattgtgag     120
gattgtgatt ttctcgattt aaagaacgtt gatagccagc ttatccagcc agaagattgg     180
gtagatcttg ctgaaactct ttacaagaat gtaaaaaaat atgatggaat tatagtcact     240
catggtaccg atactcttgc ctacacttct tcaatgataa gtttcatgct tagaaacccc     300
ccaatacccc tcgtatttac tggttctatg ataccctgcca ctgaagaaaa tagtgatgcc     360
cccctaaact tgcaaacagc aataaagttt gcaacttctg gaattagggg agtttacgtg     420
gccttcaatg gaaaagttat gcttggagtt agaacatcta aggttaggac aatgagcaga     480
gatgcattcg aaagcattaa ctaccctata attgcagaat taagaggaga gatctcgtg      540
gttaacttta ttccaaagtt taacaatgga gaagtcacat tagaccttag cacgatcca      600
aaagttctag ttataaagct aatcccagga cttttcgggg acatatttag ggcagctgta     660
gagctgggat atagaggaat tgtcatagaa ggttatggag ctggaggaat tccttatagg     720
ggaagtgatt tacttcaaac aatagaggag ctctccaagg agttccaat agtaatgaca      780
acccaggcaa tgtacgatgg agttgatcta acgaggtacg aagttgggag attagccctt     840
agagctggag taatcccagc gggggacatg acaaaagagg caacagtaac aaagctcatg     900
tggattctag ccacacaaa caatgtggaa gaaataaaag tattaatgag aaaaaatcta     960
gttggagagc ttagagatta a                                              981
```

<210> SEQ ID NO 12
<211> LENGTH: 28
<212> TYPE: DNA
<213> ORGANISM: P.furiosus

<400> SEQUENCE: 12

```
gtgcagcata tgaaaattct tctaattg                                         28
```

<210> SEQ ID NO 13
<211> LENGTH: 28
<212> TYPE: DNA
<213> ORGANISM: P.furiosus

<400> SEQUENCE: 13

```
ggcgggatcc ttaatctcta agctctcc                                         28
```

<210> SEQ ID NO 14
<211> LENGTH: 39
<212> TYPE: DNA
<213> ORGANISM: P.furiosus

<400> SEQUENCE: 14

```
ggagttgatc taacgaggta cgaagttggg agattagcc                             39
```

<210> SEQ ID NO 15
<211> LENGTH: 39

```
<212> TYPE: DNA
<213> ORGANISM: p.furiosus

<400> SEQUENCE: 15
ggctaatctc ccaacttcgt acctcgttag atcaactcc                                39

<210> SEQ ID NO 16
<211> LENGTH: 45
<212> TYPE: DNA
<213> ORGANISM: p.furiosus

<400> SEQUENCE: 16
gatttaaaga acgttgatag ccagcttatc cagccagaag attgg                         45

<210> SEQ ID NO 17
<211> LENGTH: 45
<212> TYPE: DNA
<213> ORGANISM: P.furiosus

<400> SEQUENCE: 17
ccaatcttct ggctggataa gctggctatc aacgttcttt aaatc                         45
```